United States Patent
Kramb et al.

(10) Patent No.: US 12,340,881 B2
(45) Date of Patent: Jun. 24, 2025

(54) SYSTEM AND METHOD OF PROCESSING MEDICAL IMPLANT DEVICE AND PATIENT DATA

(71) Applicant: RightDevice Inc., La Jolla, CA (US)

(72) Inventors: George A. Kramb, San Diego, CA (US); Megan C. Fenner, San Diego, CA (US); Patrick W. Frank, La Jolla, CA (US); Zhichao Han, San Diego, CA (US)

(73) Assignee: RightDevice Inc., La Jolla, CA (US)

( * ) Notice: Subject to any disclaimer, the term of this patent is extended or adjusted under 35 U.S.C. 154(b) by 65 days.

(21) Appl. No.: 17/583,180

(22) Filed: Jan. 24, 2022

(65) Prior Publication Data

US 2022/0238195 A1    Jul. 28, 2022

Related U.S. Application Data

(60) Provisional application No. 63/140,879, filed on Jan. 24, 2021.

(51) Int. Cl.
| | |
|---|---|
| *G06F 16/30* | (2019.01) |
| *G16H 10/60* | (2018.01) |
| *G16H 40/20* | (2018.01) |
| *G06F 16/33* | (2019.01) |

(52) U.S. Cl.
CPC ............ *G16H 10/60* (2018.01); *G16H 40/20* (2018.01); *G06F 16/33* (2019.01)

(58) Field of Classification Search
CPC ......... G06F 16/33; G16H 10/60; G16H 40/20
See application file for complete search history.

(56) References Cited

U.S. PATENT DOCUMENTS

| | | | |
|---|---|---|---|
| 8,799,012 B2 | 8/2014 | Butler et al. | |
| 9,491,415 B2 * | 11/2016 | Deitz | A61B 34/20 |
| 10,242,060 B2 | 3/2019 | Butler et al. | |
| 10,748,115 B2 * | 8/2020 | Laster | G16H 50/30 |
| 11,379,793 B2 * | 7/2022 | Laster | G16H 50/50 |
| 2005/0192649 A1 * | 9/2005 | Shehadeh | A61N 1/37211 |
| | | | 607/60 |

(Continued)

FOREIGN PATENT DOCUMENTS

WO    WO2007009263 A1 *   1/2007

*Primary Examiner* — Daniel A Kuddus
(74) *Attorney, Agent, or Firm* — Harter Secrest & Emery LLP

(57) ABSTRACT

A method of processing medical implant device data for preoperative patients, the method including storing, by a computer memory, a first list of medical implant devices. The method assigning, by a processor in communication with the computer memory, one or more device-variables to each of the plurality of medical implant devices, and storing, by the computer memory, one or more queries assigned to the one or more device-variables. Further, connecting a client computer with the processor and transmitting to the client computer the one or more queries. Receiving, by the processor, one or more data inputs from the client computer in response to the one or more queries. Generating, by the processor, a second list of medical implant devices as a function of the one or more data inputs received, and transmitting the second list of medical implant devices to the client computer.

15 Claims, 12 Drawing Sheets

(56) References Cited

U.S. PATENT DOCUMENTS

| | | | | |
|---|---|---|---|---|
| 2011/0295887 | A1* | 12/2011 | Palmese | G16H 20/40 |
| | | | | 707/769 |
| 2012/0116203 | A1* | 5/2012 | Vancraen | A61F 2/30942 |
| | | | | 600/407 |
| 2015/0192649 | A1* | 7/2015 | Dressler | G11B 5/3903 |
| | | | | 427/547 |
| 2016/0028998 | A1* | 1/2016 | Deitz | H04N 7/18 |
| | | | | 348/77 |
| 2016/0283676 | A1* | 9/2016 | Lyon | G06Q 40/08 |
| 2017/0199972 | A1* | 7/2017 | Hussam | G16H 10/60 |
| 2017/0201568 | A1* | 7/2017 | Hussam | H04L 67/12 |
| 2018/0122075 | A1* | 5/2018 | Deitz | A61B 5/746 |
| 2018/0310993 | A1* | 11/2018 | Hobeika | A61B 34/10 |
| 2019/0070010 | A1 | 3/2019 | McCombs | |
| 2019/0073632 | A1* | 3/2019 | Laster | G16H 20/40 |
| 2021/0092414 | A1* | 3/2021 | Karczewicz | H04N 19/18 |
| 2021/0093414 | A1* | 4/2021 | Moore | A61B 34/25 |
| 2021/0383922 | A1* | 12/2021 | Horton | G16H 40/67 |

\* cited by examiner

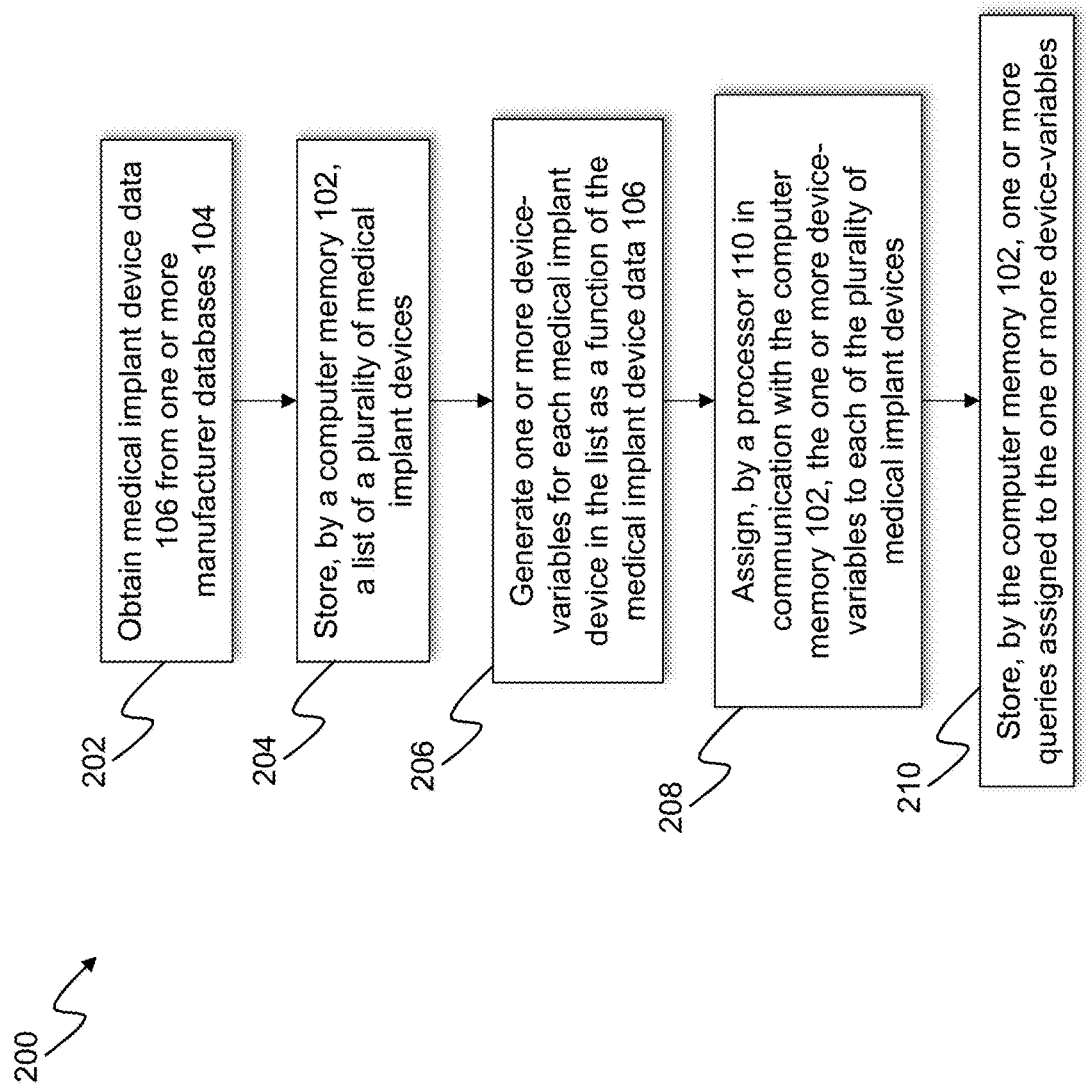

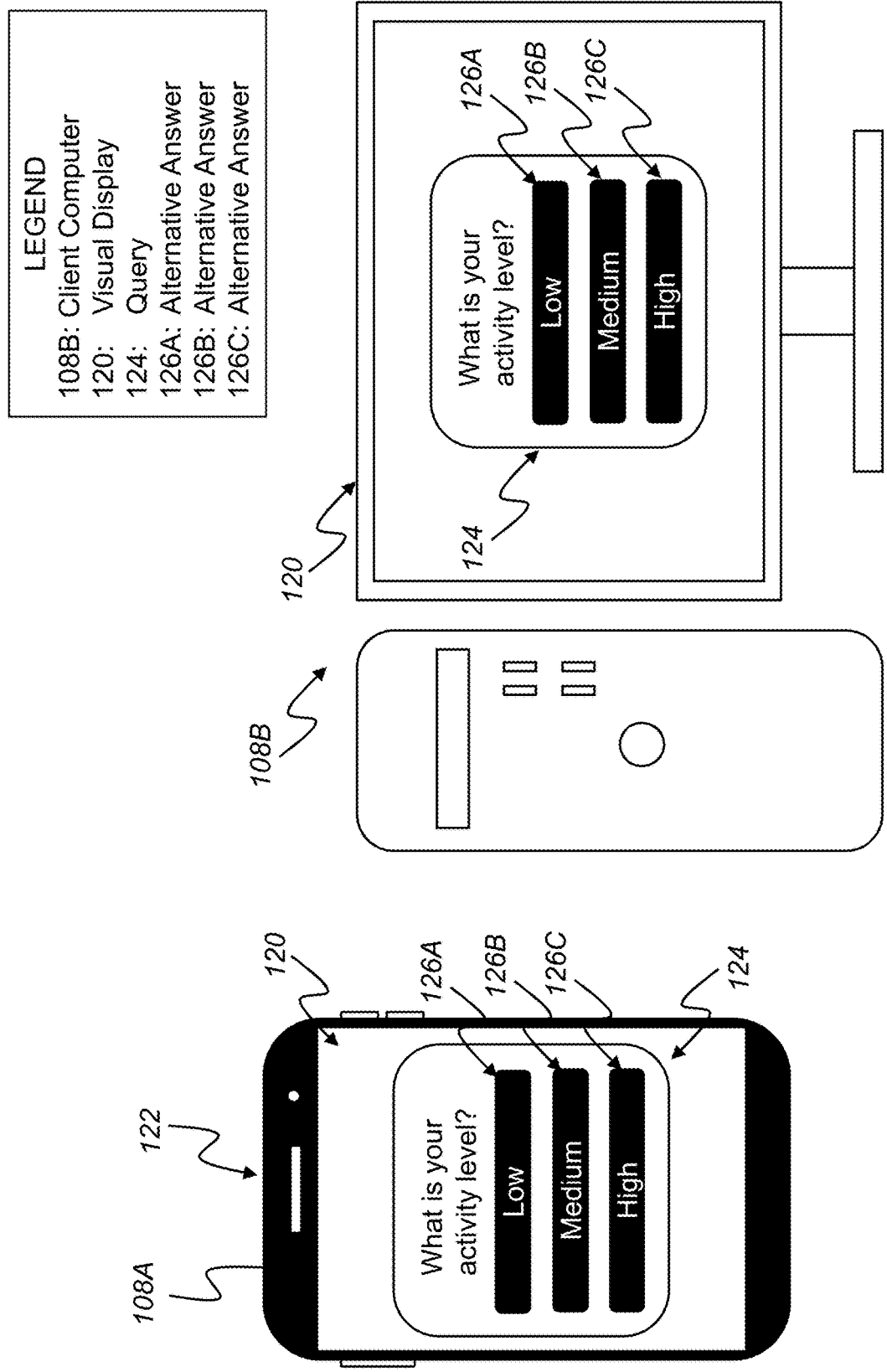

SYSTEM AND METHOD OF PROCESSING MEDICAL IMPLANT DEVICE AND PATIENT DATA

TECHNICAL FIELD

The present disclosure relates to a method, apparatus, and computer-readable medium for selecting medical implant devices for preoperative patients and/or connecting preoperative patients with a third party that has personal experience with the medical procedure for which a preoperative patient is preparing. Exemplary embodiments of the present disclosure relate to data processing of medical implant device data and otherwise facilitating or enabling informed medical procedures.

BACKGROUND

Medical care and the surgical implant of medical devices pose many decisions to the preoperative patient. Determining the appropriate medical implant device for a preoperative patient involves determining, inter alia, the preoperative patient's current health, risk factors, health goals, and the medical devices available. Health professionals in a preoperative patient's surgical support team may be constrained by time and/or experience and may be unable to provide preoperative patients with answers to technology-specific questions, post-operation expectations, and first-hand information concerning the recovery process. For example, communication between surgeons and post-operative patients may be sub-optimal and/or short in duration, and communication between surgeons and medical device manufacturers may be sub-optimal or otherwise not collaborative. These limitations produce an information deficit which can negatively affect a preoperative patient's surgical outcome. Therefore, there is a need for a system and method operable to enable, or otherwise facilitate, preoperative patients to make informed medical decisions.

SUMMARY

The present disclosure provides for a method, apparatus, and computer-readable medium for processing data.

In a first exemplary embodiment, a method of processing medical implant device data for preoperative patients includes storing, by a computer memory, a first list of medical implant devices. The method further includes assigning, by a processor in communication with the computer memory, one or more device-variables to each of the plurality of medical implant devices. The method of processing medical implant device data additionally includes storing, by the computer memory, one or more queries assigned to the one or more device-variables. Further, connecting a client computer with the processor and transmitting to the client computer the one or more queries. The method further includes receiving, by the processor, one or more data inputs from the client computer in response to the one or more queries, generating, by the processor, a second list of medical implant devices as a function of the one or more data inputs received, and transmitting the second list of medical implant devices to the client computer.

In a second exemplary embodiment, a method of connecting a patient and a patient partner includes storing, by a server having a memory and a processor, datasets of a plurality of patient partners. The method further includes connecting a client computer with said server and transmitting one or more queries to the client computer. The method of connecting a patient and a patient partner additionally include receiving, by the processor, one or more data inputs from the client computer in response to the one or more queries. Further, the method includes generating, by the processor, a list of patient partners as a function of the data inputs and transmitting the list of patient partners to the client computer.

BRIEF DESCRIPTION OF THE DRAWINGS

The accompanying drawings are incorporated herein as part of the specification. The drawings described herein illustrate embodiments of the presently disclosed subject matter and are illustrative of selected principles and teachings of the present disclosure. However, the drawings do not illustrate all possible implementations of the presently disclosed subject matter and are not intended to limit the scope of the present disclosure in any way.

FIGS. 3A and 3B present simplified diagrams of client computers according to exemplary embodiments of the present disclosure.

DETAILED DESCRIPTION

Figure 1:
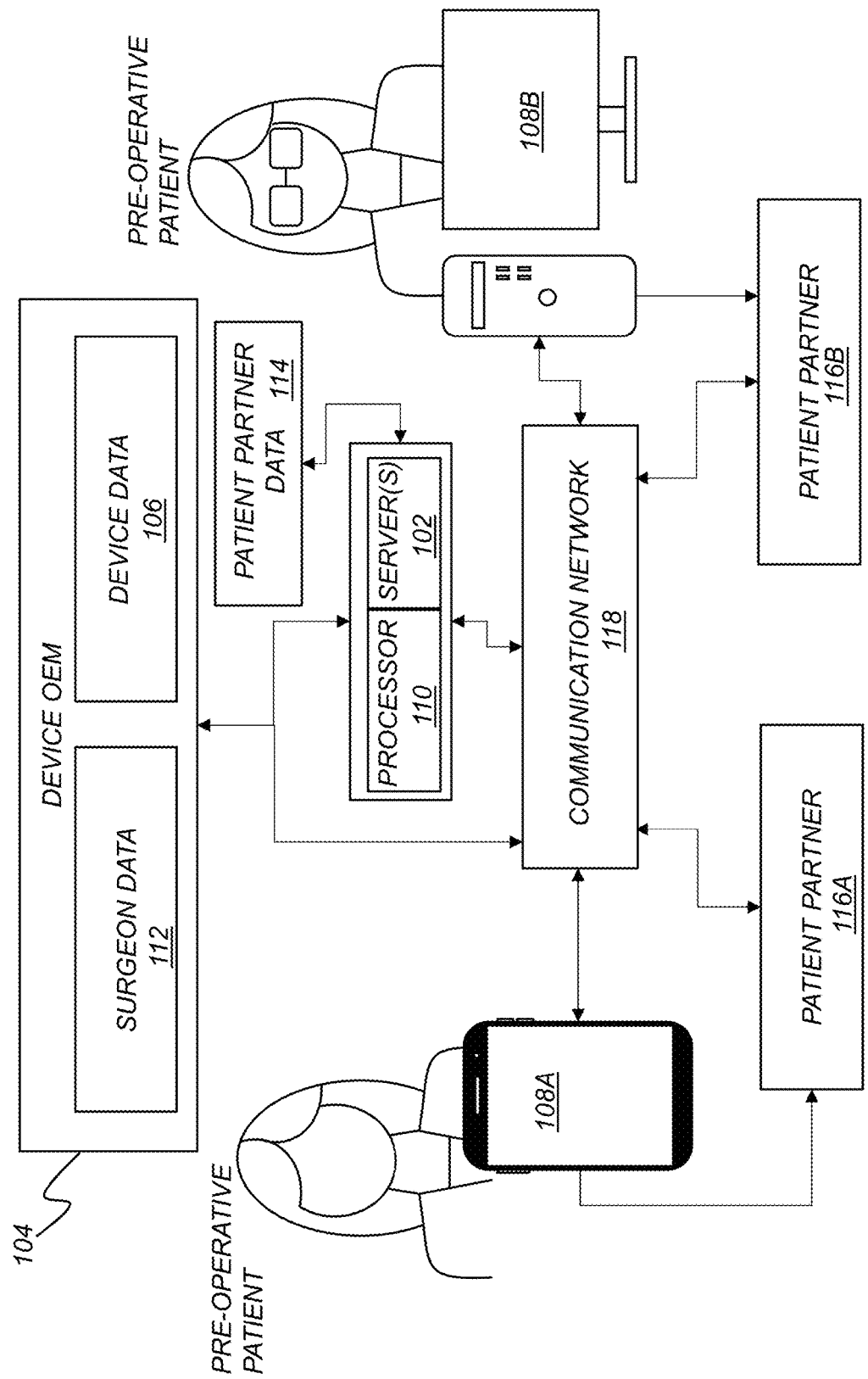
FIG. 1 presents a simplified diagram of the system environment according to an exemplary embodiment of the present disclosure.

It is to be understood that the invention may assume various alternative orientations and step sequences, except where expressly specified to the contrary. It is also to be understood that the specific assemblies and systems illustrated in the attached drawings and described in the following specification are simply exemplary embodiments of the inventive concepts defined herein. Hence, specific dimensions, directions, or other physical characteristics relating to the embodiments disclosed are not to be considered as limiting, unless expressly stated otherwise. Also, although they may not be, like elements in various embodiments described herein may be commonly referred to with like reference numerals within this section of the application.

Where they are used herein, the terms "first", "second", and so on, do not necessarily denote any ordinal, sequential, or priority relation, but are simply used to more clearly distinguish one step/element or set of steps/elements from another, unless specified otherwise.

Each year, thousands of surgical patients experience injuries or other medical concerns as a result of their medical implant devices. For each specific surgical procedure, the medical implant devices available provide patients with a widely varying post-operative experience. Different medical implant devices available for the same surgical procedure provide, inter alia, varying device longevity and expected complication rates, and enable patients to engage in different levels of post-operative activity. Selecting the appropriate medical implant device for each patient requires asking questions and having the necessary information to provide personalized answers. For example, making an informed selection of a medical implant device for a total knee replacement (i.e., knee arthroplasty) includes identifying the available knee implant devices, determining the preoperative patient's activity level, determining the preoperative patient's preference for newly developed technology, identifying the stability of the preoperative patient's knee, determining the preoperative patient's age, and determining the geographic availability of surgeons able to perform the surgical procedure with a specific knee implant device. Medical implant devices are not one size fits all and personalizing the selection of a patient's medical implant device reduces the potential for issues therewith.

Figure 2B:
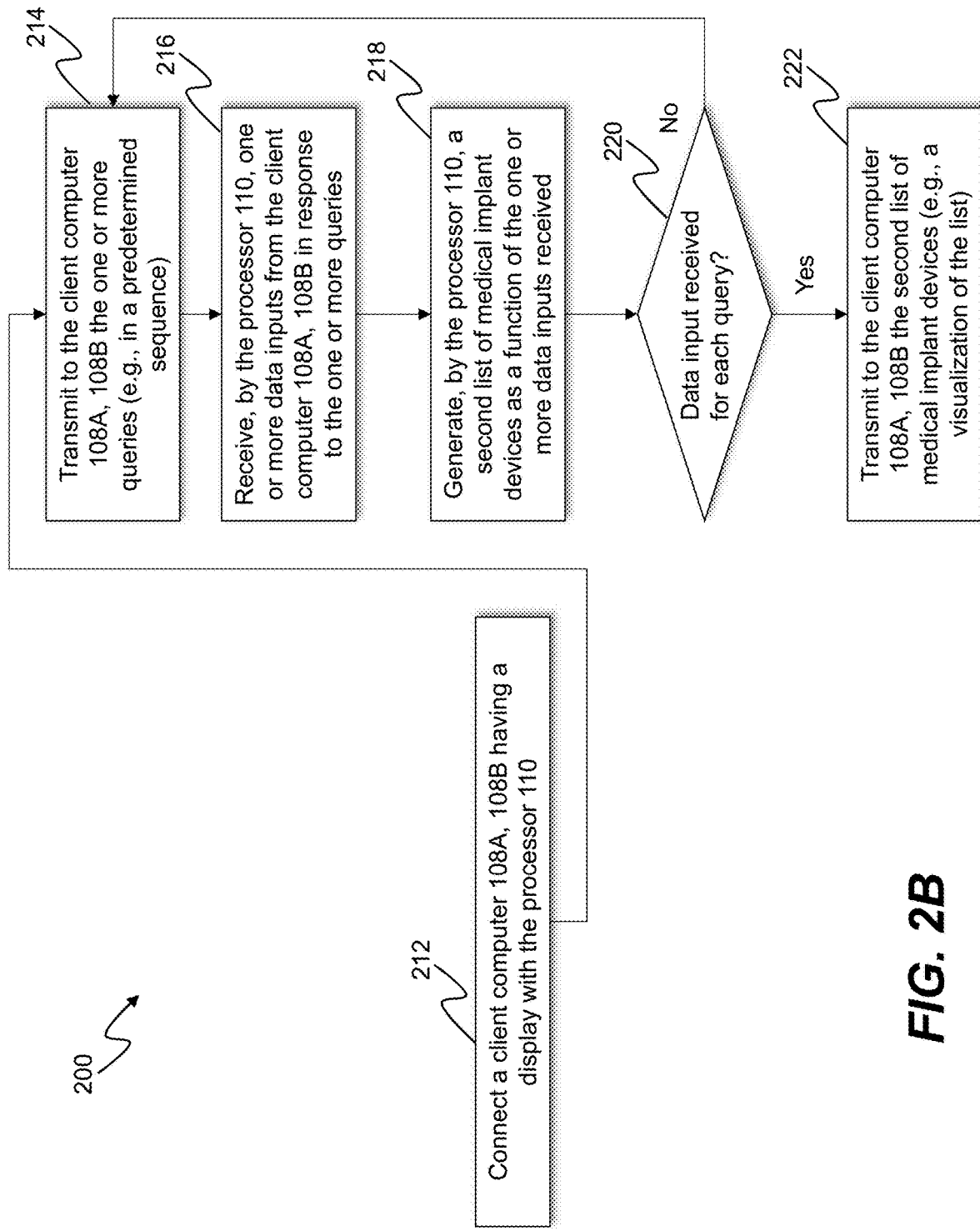
FIG. 2 presents a flow chart of a method of processing medical implant device data according to an exemplary embodiment of the present disclosure.
Figure 6:
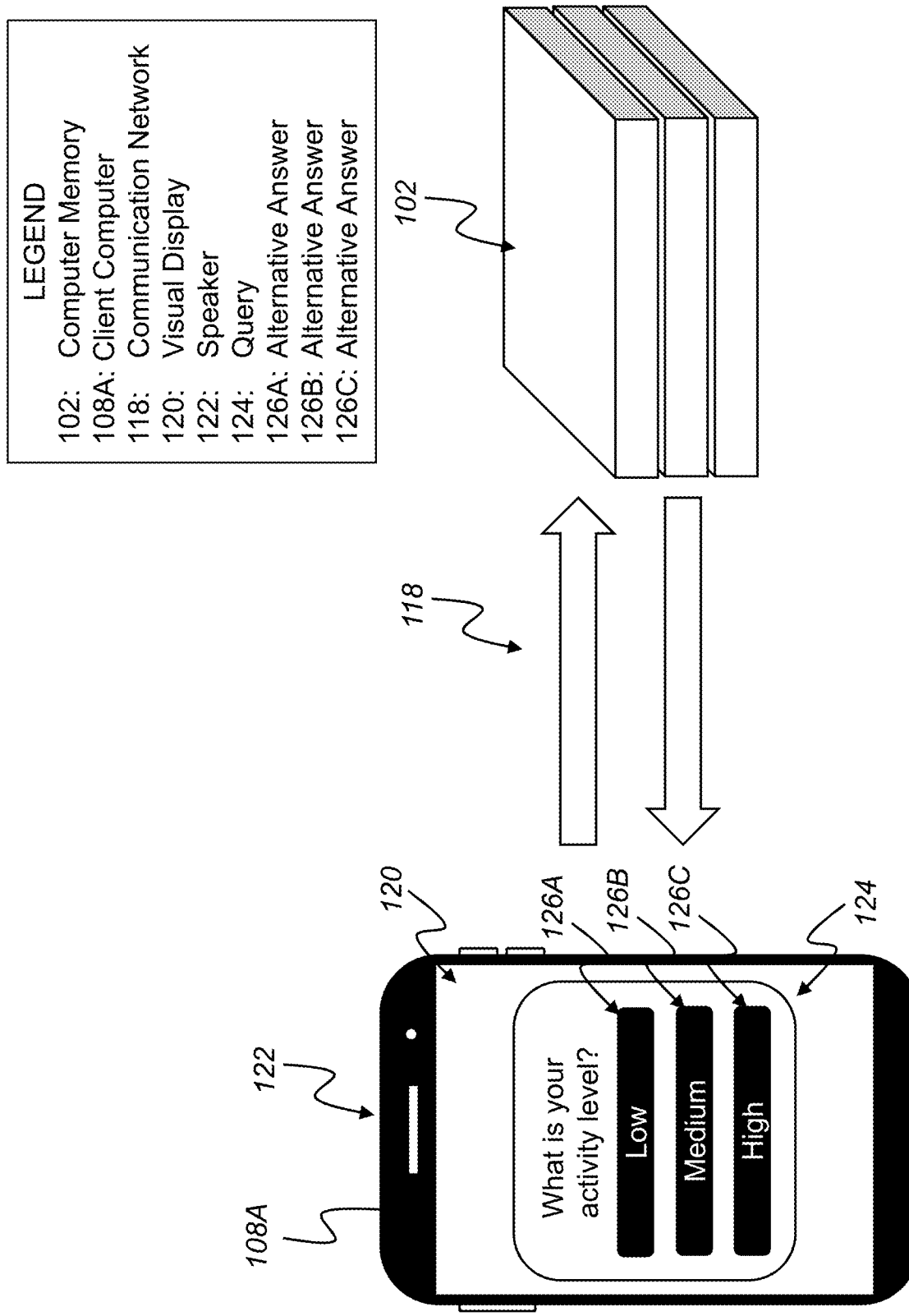
FIG. 6 presents a simplified diagram of a portion of the system environment according to an exemplary embodiment of the present disclosure.

Referring now to FIGS. 1, 2, and 6, presented is an exemplary embodiment of a method of medical implant device data processing 200. The method 200 begins at block 202 by obtaining the technical data 106 and/or specifications of one or more medical implant devices from their original equipment manufacturers (OEMs). In an embodiment, the medical implant device technical data 106 is acquired from OEM web pages 104 and/or databases 104 by web data extraction and stored on one or more servers 102 (e.g., a first computer memory). Persons skilled in the relevant arts will recognize that additional methods of data acquisition may be utilized in conjunction with web data extraction, or instead of web data extraction, to obtain the medical implant device technical data 106. For example, the medical implant device technical data 106 may also be obtained via manual data acquisition.

The method 200 continues at block 204 by storing a list of medical implant devices at the one or more servers 102. For example, the list of the medical implant devices may include only those medical implant devices for which medical implant device technical data 106 was obtained in the previous step at block 202. However, the list of medical implant devices may also include medical implant devices for which device data 106 has previously been downloaded, uploaded, or otherwise transferred to the one or more servers 102.

At block 206, the method 200 continues by generating one or more device-variables for each medical implant device in the list as a function of the medical implant device technical data 106. For example, the device-variables may include, but are not limited to, device type, device material(s), device range of motion, device lifespan, patient gender, patient age, patient height, patient preexisting conditions, and device weight rating (e.g., acceptable patient weight range). In an embodiment, the device-variables are extracted or otherwise obtained from the medical implant device technical data 106. The device-variables generated for the medical implant devices may also be produced as a function of a preexisting list of device-variables stored on the servers 102. In an embodiment, not all device-variables of the preexisting list are applicable to all medical implant devices. For example, the device-variables generated at block 206 for knee arthroplasty implants may be different than the device-variables generated at block 206 for total hip arthroplasty implants. The method 200 continues at block 208 by assigning the device-variable values for each of the corresponding medical implant devices to each of the corresponding medical implant devices utilizing a processor 110 in signal communication with the servers 102.

At block 210, the method 200 includes storing one or more queries (e.g., questions) assigned to the one or more device-variables at the one or more servers 102. As described below, assigning one or more queries to the device-variables facilitates filtering the available medical implant devices into a set of medical implant devices having technical specifications that meet the requirements of a particular patient.

At block 212, the method of medical implant device data processing 200 continues by connecting a client computer 108A, 108B (e.g., a preoperative patient's smartphone, tablet, personal computer, or other computer device) with the one or more servers 102. In an embodiment, the client computer 108A, 108B includes a visual display 120 or monitor operable to generate and display images to a user. As shown at block 214, the method 200 continues by presenting the one or more queries 124 assigned to the device-variables to the preoperative patient in a predetermined sequence. In another embodiment, the queries 124 are not presented in a predetermined sequence. The display 120 of the client computer 108A, 108B may be utilized to present the queries 124. However, persons skilled in the art will recognize that the client computer 108A, 108B may include other apparatuses operable to present the queries 124 to the preoperative patient. For example, the client computer 108A, 108B may include an audio loudspeaker 122 operable to produce the queries 124 in audible format.

The preoperative patient, through the client computer 108A, 108B, can answer the queries 124. At block 216, the method 200 continues by receiving, by the processor 110, one or more data inputs from the client computer 108A, 108B in response to the one or more queries 124. As illustrated in FIGS. 3A-3B, in an embodiment, the queries 124 are presented as multiple choice questions with two or more alternative answers 126A, 126B, 126C which the preoperative patient can select, thereby transmitting a data input from the client computer 108A, 108B to the processor 110. In an embodiment, the preoperative patient may transmit a free-response answer to the processor 110 in response to each query 124. Where a free-response answer is transmitted, the processor 110 may perform a keyword search to identify terms corresponding to the device-variables.

The method 200 continues at block 218 by generating, via the processor 110, a second list of medical implants devices as a function of the one or more data inputs received at block 216. For example, a query 124 may be assigned to the device-variable "range of motion," and utilized in processing data concerning knee arthroplasty. The device-variable "range of motion," may be categorized in the server 102 as small, medium, and large ranges of motion. In this example, medical implant devices utilized in total knee replacement might be considered to have a small range of motion at typical flexion of less than 115°, a medium range of motion at typical flexion of 116°-125°, and a large range of motion at typical flexion of greater than 126° after implantation. At block 210, the query 124 assigned to the device-variable "range of motion" may be "Activity Level?", and the data input received by the processor 110 from the client computer 108A, 108B may be one of the multiple choice answers "low" 126A, "medium" 126B, and "high" 126C, with the answer "low" 126A corresponding to small range of motion, "medium" 126B corresponding to medium range of motion, and "high" 126C corresponding to large range of motion. If the preoperative patient were to transmit the data input of the multiple choice answer "high" 126C to the processor 110 via the client computer 108A, 108B, the processor 110 then generates a second list of medical implant devices as a function of the stored list of all knee implant devices that would be operable to provide the preoperative patient a large range of motion after implantation.

In an embodiment, at block 220, the method 200 includes determining whether a data input has been received for each query 124. If a data input has been received for each query 124, the method 200 continues at block 222 by transmitting to the client computer 108A, 108B the second list of medical implant devices. If a data input has not been received for each query 124, the method 200 returns to block 214 and transmits one or more queries 124 to the client computer 108A, 108B.

In an embodiment, at block 214 the queries 124 may be transmitted to the client computer 108A, 108B in a non-sequential manner (e.g., all at once). In such an embodiment, the data input received by the processor 110 would not necessarily be received in a specific order. At block 218, when the method 200 generates a second list of medical implant devices, the queries 124 may be weighted such that certain data input is considered of higher value when the processor 110 generates the second list of medical implant devices. For example, the data input corresponding to a query 124 concerning the patient's material sensitivity/allergies may be weighted more than a query 124 concerning the patient's activity level, such that the second list generated by the processor 110 may not include all or any knee implant devices, for example, having a large range of motion after implantation.

In an embodiment, at block 214 the queries 124 may be transmitted to the client computer 108A, 108B in a sequential manner. In such an embodiment, the data input received by the processor 110 may be processed and a second list of medical implant devices generated as a function of the data input received in response to a first query 124. A second query 124 may then be transmitted to the client computer 108A, 108B as a function of the second list. For example, where the first query 124 concerns the preoperative patient's metal sensitivity, and the corresponding data input indicates that patient has a metal sensitivity, the second list of medical implant devices suited for the patient's needs may not include any additional device-variables such as weight rating, age range, and/or preference for new technologies. Thus, the second list generated is transmitted to the client computer 108A, 108B at block 222. However, if the corresponding data input indicates that patient does not have a metal sensitivity, the second list of medical implant devices suited for the patient's needs may include additional device-variables such as weight rating, age range, and/or preference for new technologies, and a second query 124 is transmitted to the client computer 108A, 108B at block 214.

Figure 7A:
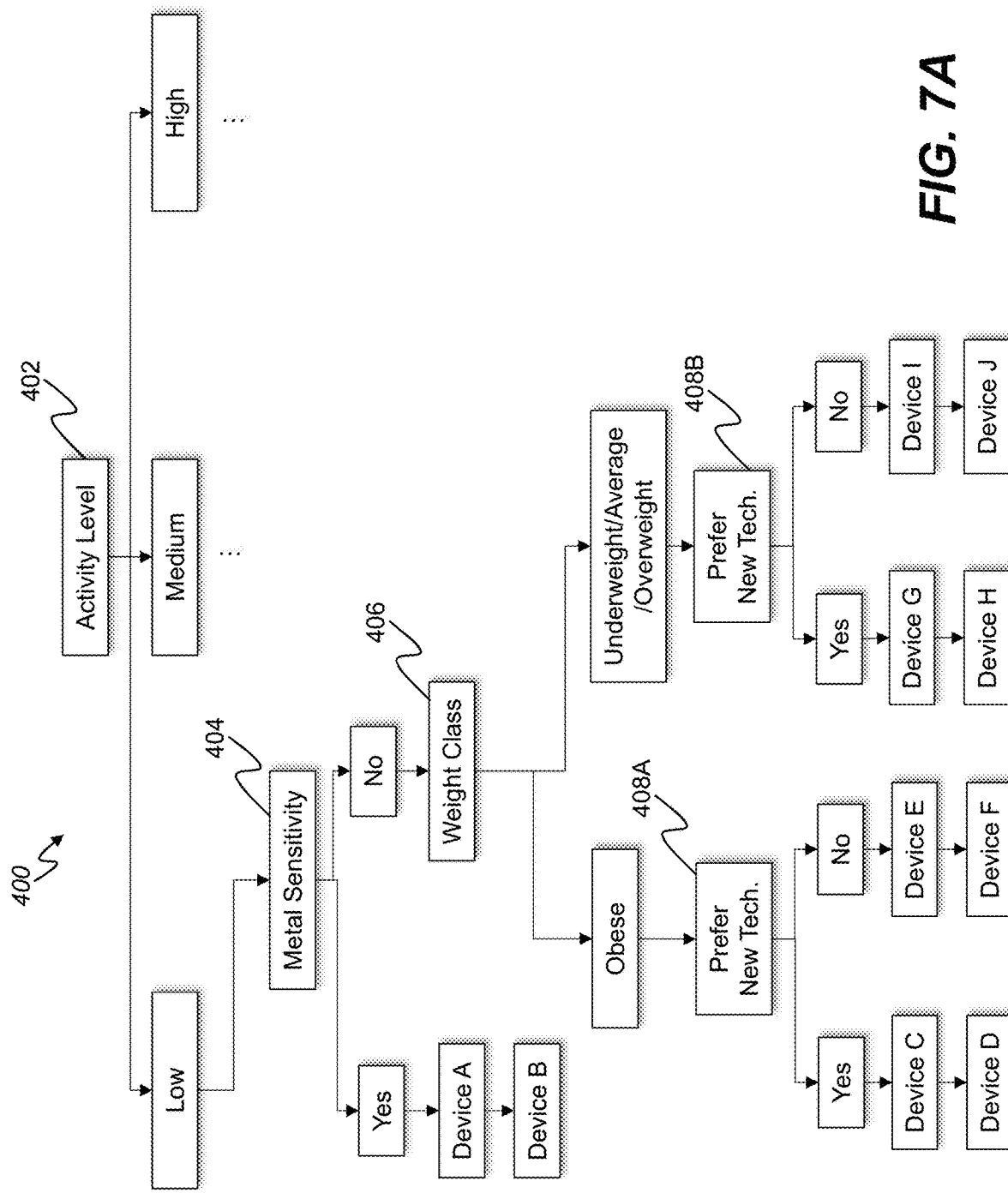
FIGS. 7A-7C present a flow chart of queries and data inputs corresponding to one or more medical implant device-variables according to an exemplary embodiment of the present disclosure.
Figure 7B:
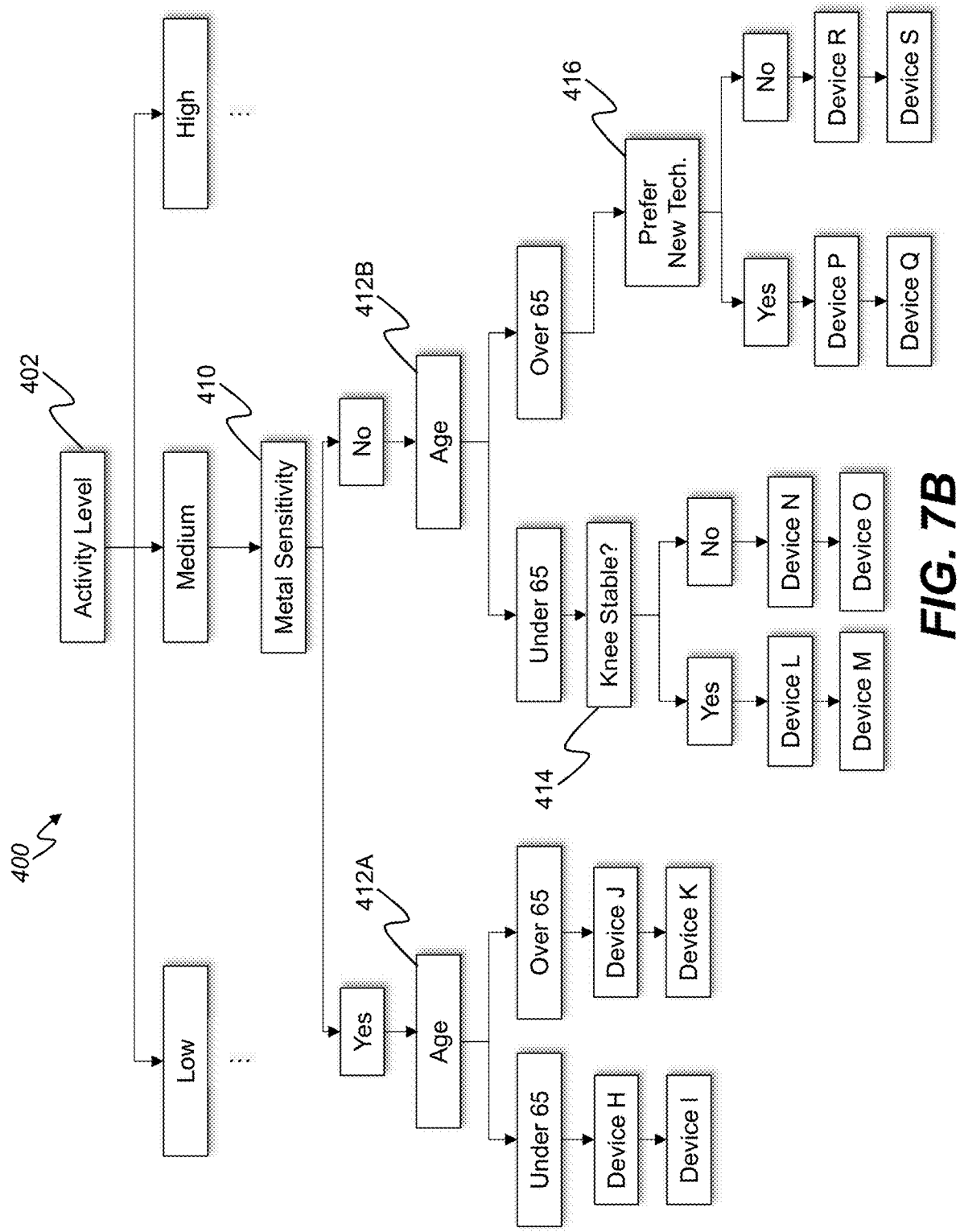
Figure 7C:
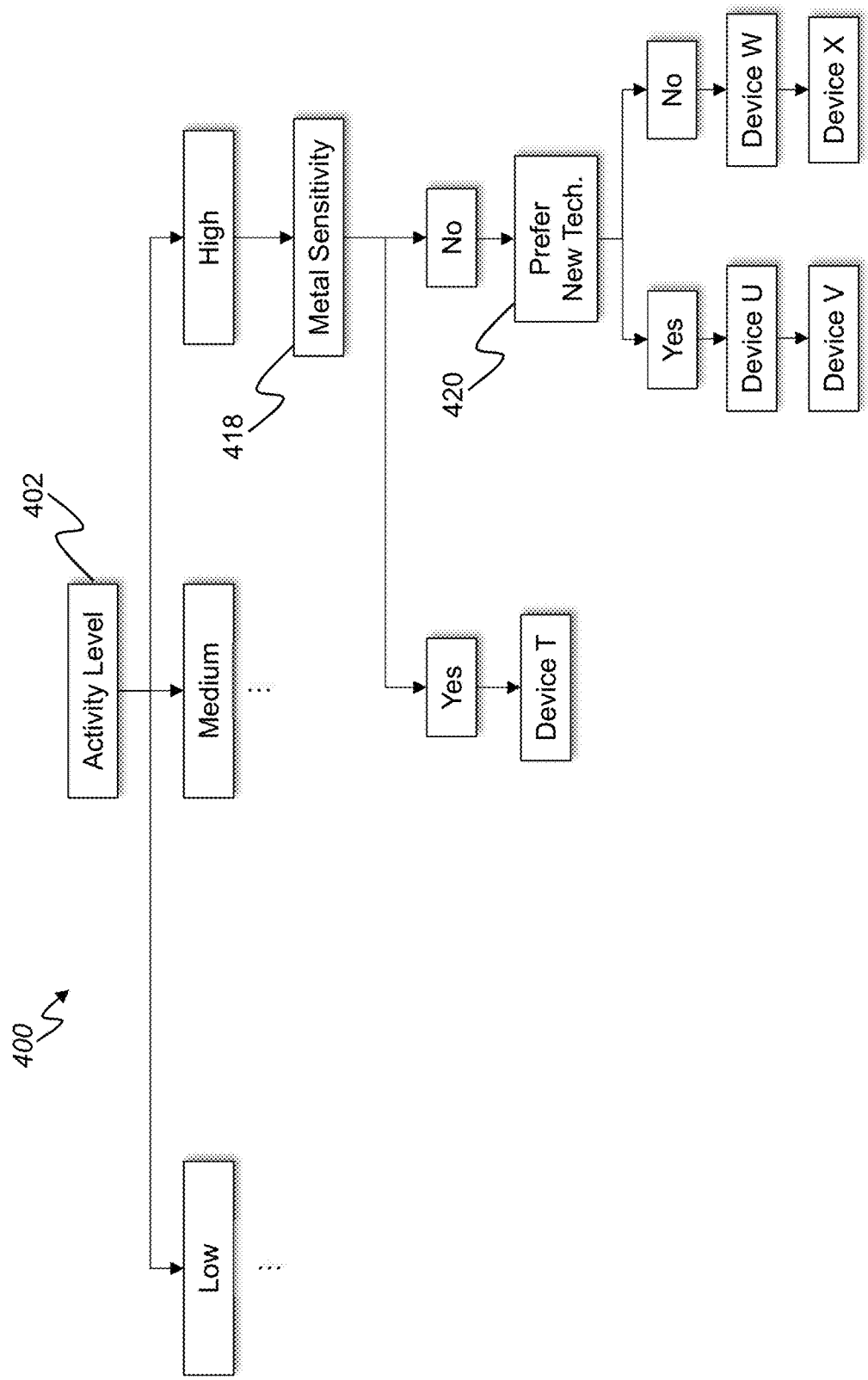

In an embodiment, as illustrated in FIGS. 7A-7C, the queries 124 and data inputs corresponding to one or more medical implant device-variables at blocks 210-220 of the method 200 may comprise, but are not limited to, preoperative patient activity level 402, preoperative patient material sensitivity 404, 410, 418 (e.g., metal sensitivity), preoperative patient age 412A, 412B, preoperative patient knee stability 414, preoperative patient weight classification 406, and preoperative patient preference for new technology 408A, 408B, 416, 420. Additionally, the queries 124 may also concern the propensity of the joint in question to dislocate, graft type, and preference for a permanent or absorbable device/graft as a function of the medical procedure considered.

In an embodiment, the method of medical implant device data processing 200 includes an integrated user feedback component utilized to update the list of medical implant devices stored on the servers 102. For example, after a predetermined period of time, and/or after receiving input from a patient that their surgical procedure has been completed, the processor 110 may transmit a query 124 to the client computer 108A, 108B comprising a multiple choice answer in the form of two or more levels of satisfaction with their medical implant device. Upon receiving the data input corresponding to the patient's level of satisfaction, the processor 110 amends a device-variable value corresponding to the device's ranking. As a result, medical implant devices in a list generated at block 218 may be listed in order of patient satisfaction.

Figure 4A:
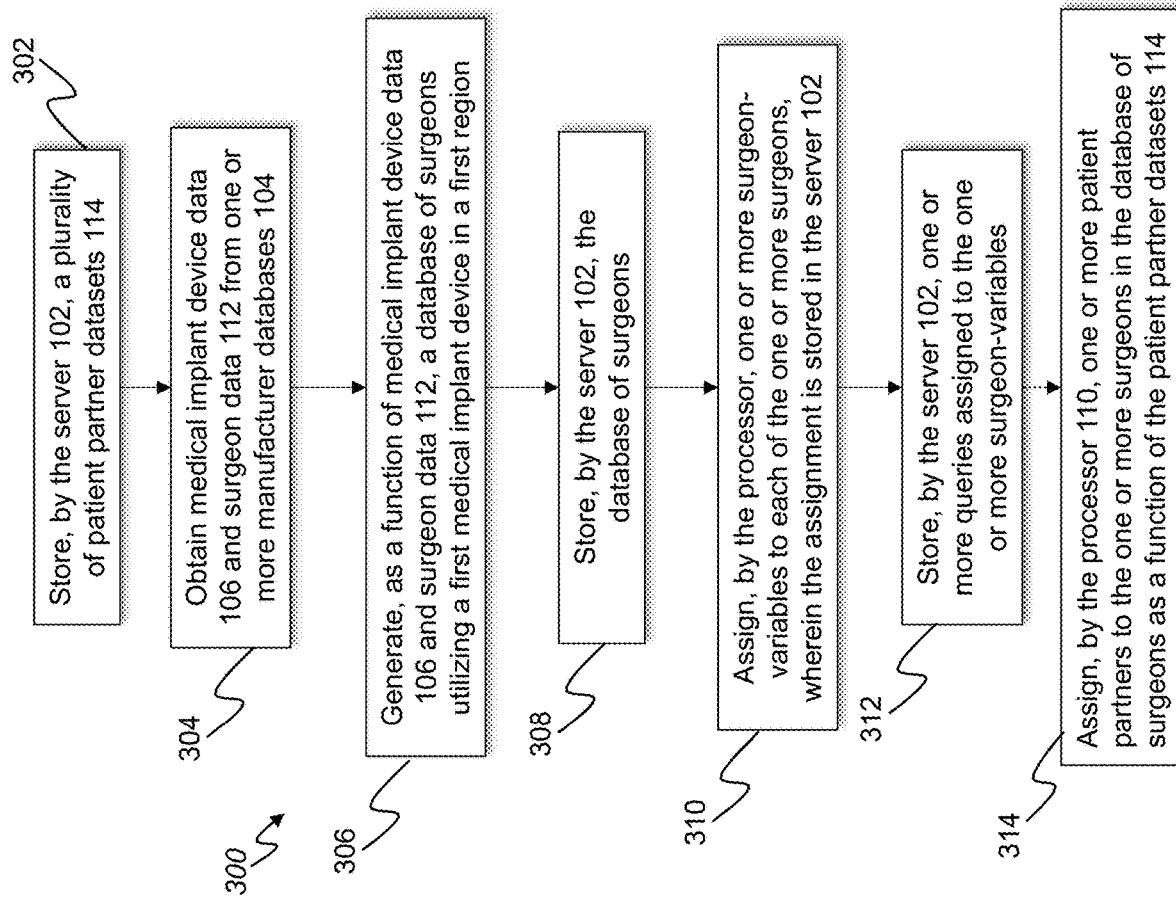
FIGS. 4A-4B present flow charts of a method of processing patient partner data and surgeon data according to an embodiment of the present disclosure.
Figure 4B:
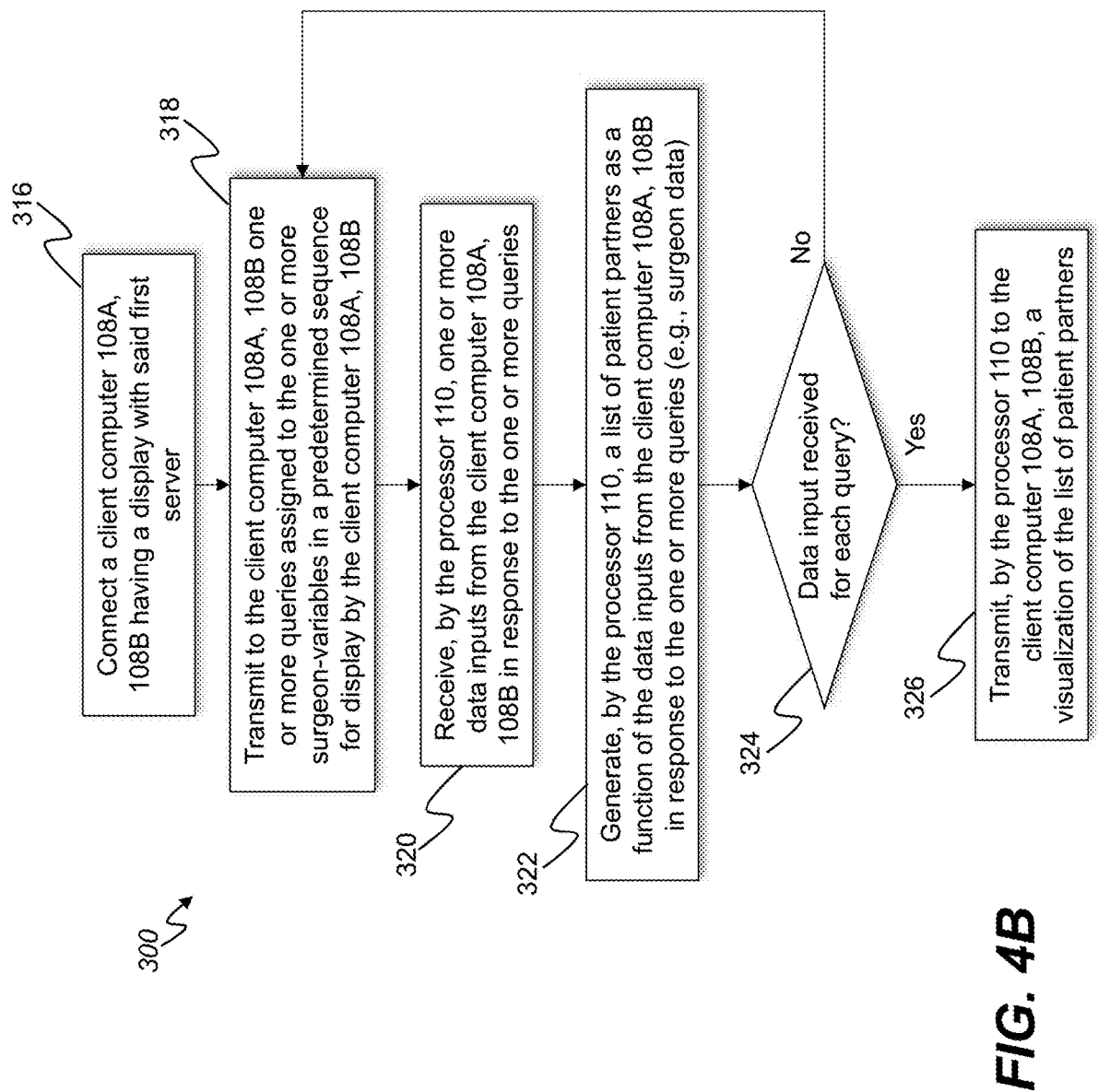

Referring now to FIGS. 1 and 4A-4B, presented is an exemplary embodiment of a method of data processing 300. As indicated at block 302, the method 300 includes storing a plurality of patient partner datasets 114 in the servers 102. In an embodiment, patient partners 116A, 116B are third parties who have received and recovered from medical device implant surgeries. However, patient partners 116A, 116B may be third persons with other forms of first-hand experience with one or more medical concerns. Patient partners 116A, 116B provide preoperative patients an opportunity to converse with someone having first-hand experience with their selected medical procedure, surgeon and/or medical implant device. Post-operative patients may become patient partners 116A, 116B by electing to join the patient partner program. In many cases, post-operative patients are invited/recommended to join the patient partner program by their surgeon.

As illustrated in FIG. 4B, in an embodiment, the method 300 at block 304 includes obtaining the technical data 106 and/or specifications of one or more medical implant devices from their original equipment manufacturers (OEMs) and surgeon data 112 from the OEM. In an embodiment, the medical implant device technical data 106 and surgeon data 112 is acquired from OEM web pages 104 and/or databases 104 by web data extraction and stored on one or more servers 102 (e.g., a first computer memory). Persons skilled in the relevant arts will recognize that additional methods of data acquisition may be utilized in conjunction with web data extraction, or instead of web data extraction, to obtain the medical implant device technical data 106. For example, the medical implant device technical data 106 may also be obtained via manual data acquisition.

The method 300 continues at block 306 by generating a database of surgeons currently trained to surgically implant a first medical implant device (e.g., a knee arthroplasty implant) and operating within a first geographic region (e.g., the San Diego metropolitan area). The database of surgeons may be generated via the processor 110 as a function of the medical implant device data 106 and the surgeon data 112 obtained at block 304. However, the database of surgeons may also be generated as a function of medical implant device data 106 and the surgeon data 112 that has previously been downloaded, uploaded, or otherwise transferred to the one or more servers 102.

At block 308, the method 300 continues by storing the database of surgeons on the servers 102. The method 300, at block 310, includes assigning one or more surgeon-variables to each of the one or more surgeons via the processor 110, wherein the assignment is stored in the servers 102. For example, the surgeon-variables may include, but are not limited to, number of years in surgical practice, number of specific medical implant device procedures performed, geographic location, and surgical specialty. In an embodiment, the surgeon-variables are extracted or otherwise generated from the surgeon data 112 obtained at block 304. Although only one geographic region and one medical implant device type may be referred to with regard to the method 300 for clarity of description, the database of surgeons generated in the method 300 will generally include multiple geographic regions and multiple medical implant device types. Similarly, some surgeons may be assigned to more than one medical implant device in the servers 102.

The method 300 continues at block 312 by storing one or more queries (e.g., questions) assigned to the one or more surgeon-variables at the one or more servers 102. Assigning one or more queries to the surgeon-variables facilitates filtering the available surgeons into a set of surgeons that meet the requirements of a particular patient. At block 314, assigning one or more patient partners 116A, 116B to the one or more surgeons in the database of surgeons as a function of the patient partner datasets.

As illustrated in FIG. 4B, the method 300 connects a client computer 108A, 108B with the servers 102 at block 316, and transmits one or more queries to the client computer 108A, 108B at block 318. At block 320, the processor 110 receives one or more data inputs from the client computer 108A, 108B in response to the queries. Then at block 322, generating a list of patient partners 116A, 116B as a function of the data input.

In an embodiment, at block 324, the method 300 includes determining whether a data input has been received for each query transmitted at block 318. If a data input has been received for each query, the method 300 continues at block 326 by transmitting to the client computer 108A, 108B the list of patient partners 116A, 116B. If a data input has not been received for each query, the method 300 returns to block 318 and transmits one or more queries to the client computer 108A, 108B.

Figure 4C:
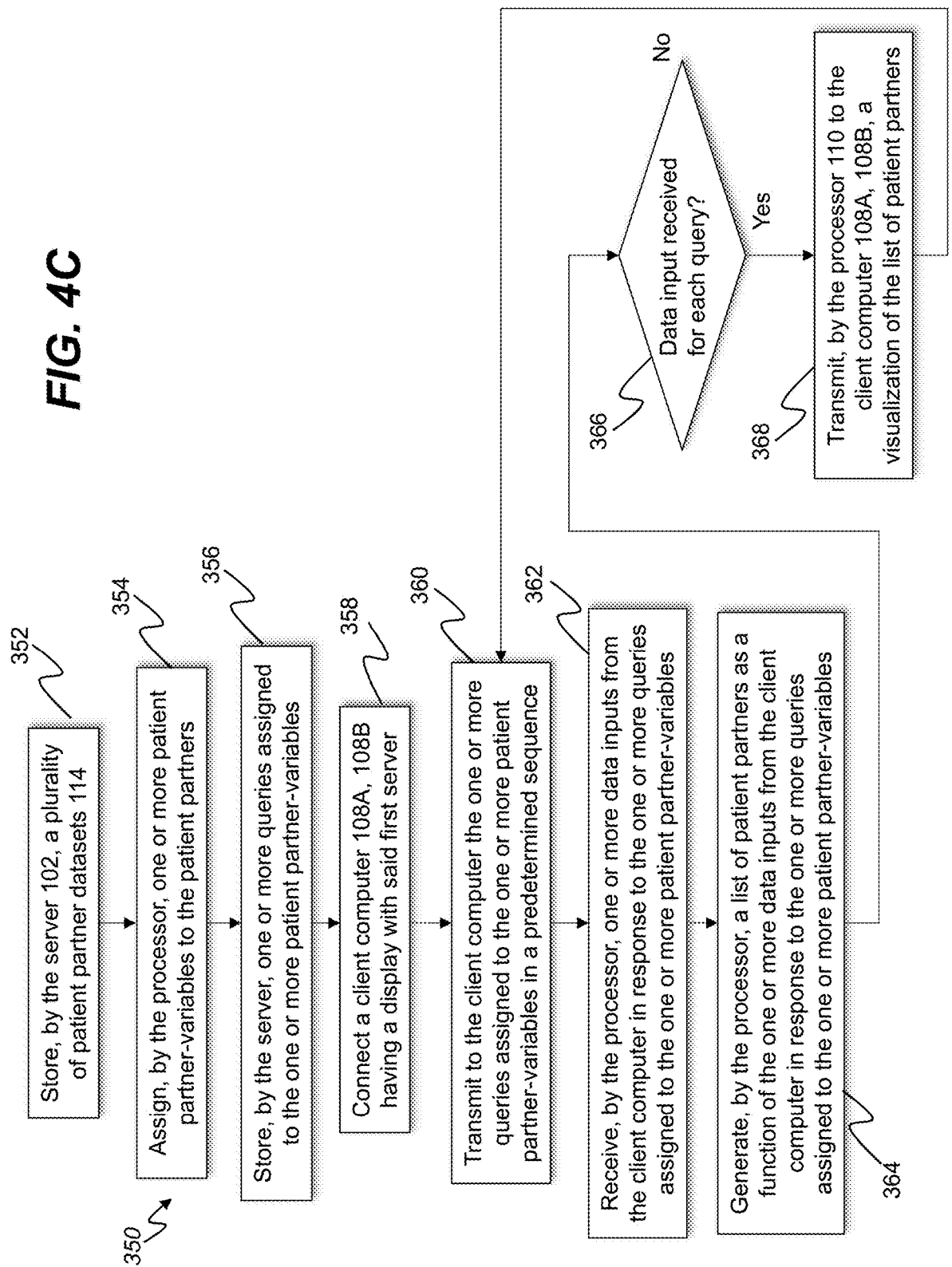
FIG. 4C presents a flow chart of a method of processing patient partner data according to an embodiment of the present disclosure.

In an embodiment, as illustrated in FIGS. 1 and 4C, a method 350, at block 352, stores a plurality of patient partner datasets 114 in the servers 102 as in the method 300. At block 354, the method 350 assigns patient partner-variables to the patient partners 116A, 116B. The method 350 continues at block 356 by storing one or more queries assigned to the one or more patient partner-variables at the one or more servers 102. At block 358, the method 350 connects a client computer 108A, 108B with the one or more servers 102. Next, the queries transmitted to the client computer at block 360 include one or more queries assigned to the one or more patient partner-variables and the data inputs received, by the processor, at block 362 include one or more data inputs from the client computer in response to the one or more queries assigned to the one or more patient partner-variables. At block 364, the method 350 generates a list of patient partners 116A, 116B as a function of the data input.

The method 350, at block 366, includes determining whether a data input has been received for each query transmitted at block 360. If a data input has been received for each query, the method 350 continues at block 38 by transmitting to the client computer 108A, 108B the list of patient partners 116A, 116B. If a data input has not been received for each query, the method 350 returns to block 360 and transmits one or more queries to the client computer 108A, 108B.

In an embodiment, at block 318, 360 the queries may be transmitted to the client computer 108A, 108B in a sequential manner. In such an embodiment, the queries earlier in the sequence may be directed to evoking data input which enables the filtering of surgeons in the database of surgeons. For example, initial queries may prompt data input concerning, for example, the type of surgery in question and the geographic location of the preoperative patient. At block 322 the method 300 continues by generating a list of surgeons as a function of the one or more data inputs via the processor 110. Following queries may then be directed to prompt data input concerning, for example, the pre-operative patient's surgical experience, preferred gender of a patient partner, the pre-operative patient's age, and the pre-operative patient's activity level. Then generating a list of patient partners 116A, 116B as a function of the list of surgeons and data input.

Figure 5:
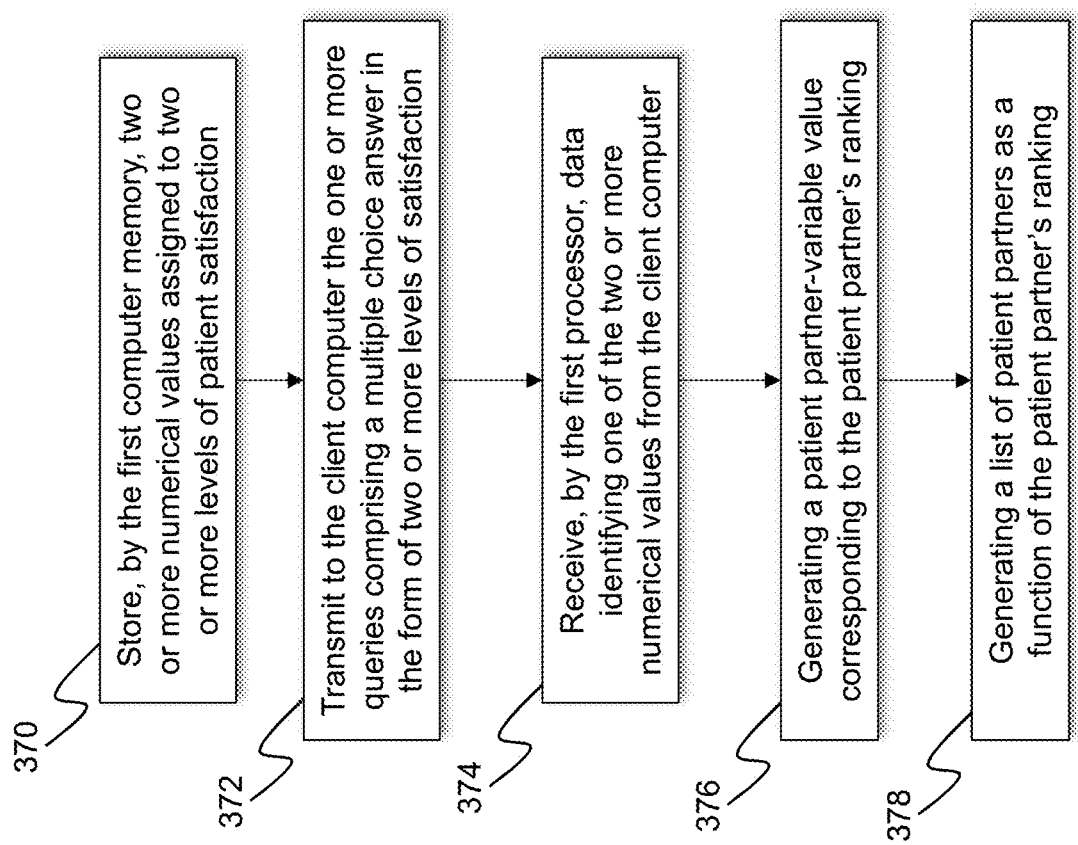
FIG. 5 presents a flow chart of a method of patient feedback according to an embodiment of the present disclosure.

In an embodiment, as illustrated in FIG. 5, the methods 300, 350 include an integrated user feedback component utilized to update the list of patient partners 116A, 116B stored on the servers 102. For example, at block 370 the server 102 may store two or more numerical values assigned to two or more levels of patient satisfaction. After a predetermined period of time, and/or after receiving input from a patient that their surgical procedure has been completed, at block 372 the processor 110 may transmit a query to the client computer 108A, 108B comprising a multiple choice answer in the form of two or more levels of satisfaction with their patient partner 116A, 116B. At block 374, upon receiving the data input corresponding to the patient's level of satisfaction, the processor 110 amends a patient partner-variable value corresponding to the patient partner's ranking at block 376. As a result, patient partners 116A, 116B in a list generated at block 326, 368 may be listed in order of patient satisfaction (i.e., ranking) at block 378.

As illustrated in FIGS. 1 and 6, in an embodiment, the servers 102 and processor 110 are in direct or indirect signal communication with the client computers 108A, 1086, the OEM web pages 104 and/or databases 104, and the patient partners 116A, 1166 via the communication network 118. Exemplary embodiments of servers 102 are also able to manipulate, manage, transmit, receive, and edit data files maintained within its memory or located on its hard disk. Exemplary embodiments of the communication network 118 include a LAN, WAN (e.g., the internet), public networks, and private networks.

One or more features of the embodiments described herein may be combined to create additional embodiments which are not depicted. While various embodiments have been described in detail above, it should be understood that they have been presented by way of example, and not limitation. It will be apparent to persons skilled in the relevant arts that the disclosed subject matter may be embodied in other specific forms, variations, and modifications without departing from the scope, spirit, or essential characteristics thereof. The embodiments described above are therefore to be considered in all respects as illustrative, and not restrictive. The scope of the invention is indicated by the appended claims, and all changes that come within the meaning and range of equivalents thereof are intended to be embraced therein.

What is claimed is:

1. A computer-implemented method, including a hardware processor, of processing medical implant device data for preoperative patients, the method comprising:
   providing a first computer memory in communication with a first hardware processor;
   obtaining medical implant device data from a manufacturer database via web data extraction;
   generating one two or more device-variables as a function of the medical implant device data, wherein the two or more device-variables include a preoperative patient preference for new technology;

creating a first list of medical implant devices via the first hardware processor;

storing, by the first computer memory, the first list of medical implant devices;

assigning, by the first hardware processor, the two or more device-variables to each of the plurality of medical implant devices;

storing, by the first computer memory, one or more queries assigned to the two or more device-variables;

connecting a remote client computer, accessible by an instruction of the preoperative patient, with the first hardware processor;

transmitting to the client computer the one or more queries;

receiving, by the first hardware processor, one or more data inputs from the client computer in response to the one or more queries, wherein the one or more data inputs are assigned a weighted value;

generating, by the first hardware processor, a second list of medical implant devices as a function of the one or more data inputs received and their weighted values; and transmitting to the client computer the second list of medical implant devices.

2. The computer-implemented method according to claim 1, wherein the step of transmitting to the client computer the second list of medical implant devices further comprises transmitting a visualization of the second list of medical implant devices for presentation via a display of the client computer.

3. The computer-implemented method according to claim 1, wherein the one two or more device-variables comprise preoperative patient activity level, preoperative patient material sensitivity, preoperative patient age, and preoperative patient weight classification.

4. The computer-implemented method according to claim 1, wherein the one or more queries are transmitted to the client computer in a predetermined sequence.

5. The computer-implemented method according to claim 1, further comprising receiving a first variable in response to a first query, and generating the second list of a plurality of medical implant devices as a function of the first variable.

6. The computer-implemented method according to claim 1, further comprising storing, by the first computer memory, two or more numerical values assigned to two or more levels of patient satisfaction; receiving, by the first hardware processor, data identifying one of the two or more numerical values from the client computer; and revising the weighted values assigned to the one or more data inputs as a function of the two or more numerical values.

7. A computer-implemented method of connecting a patient and a patient partner, the method comprising:
storing, by a server having a memory and a processor, datasets of a plurality of patient partners comprising recovered postoperative patients;

obtaining, by the server, medical implant device data and surgeon data from one or more manufacturer databases, and generating, as a function of medical implant device data and surgeon data, a database of surgeons;

assigning, by the processor, one or more patient partners to the one or more surgeons in the database of surgeons as a function of the patient partner datasets;

connecting a client computer, accessible by an instruction of the patient, with the first server;

transmitting to the client computer one or more queries;

receiving, by the processor, one or more data inputs from the client computer in response to the one or more queries;

generating, by the processor, a list of patient partners as a function of the data inputs; and transmitting to the client computer the list of patient partners.

8. The method according to claim 7, further comprising:
storing, by the server, a database of surgeons utilizing a first medical implant device in a first region;

assigning, by the processor, one or more surgeon-variables to each of the one or more surgeons;

storing, by the server, one or more queries assigned to the one or more surgeon-variables;

transmitting to the client computer the one or more queries assigned to the one or more surgeon-variables; and receiving, by the processor, one or more data inputs from the client computer in response to the one or more queries assigned to the one or more surgeon-variables, wherein the list of patient partners is generated as a function of the data inputs from the client computer in response to the one or more queries assigned to the one or more surgeon-variables.

9. The method according to claim 8, further comprising generating, by the processor, a list of surgeons as a function of the one or more data inputs from the client computer; and generating, by the processor, a list of patient partners as a function of the list of surgeons.

10. The method according to claim 7, further comprising assigning, by the processor, a surgeon in the database of surgeons to one or more medical implant devices, wherein the assignment is stored in the server memory.

11. The method according to claim 7, further comprising storing, by the server memory, two or more numerical values assigned to two or more levels of patient satisfaction; and receiving, by the first processor, a data input identifying one of the two or more numerical values from a second client computer.

12. The method according to claim 7, wherein the one or more queries comprise at least two queries transmitted to the client computer in a predetermined sequence.

13. The method according to claim 7, further comprising:
assigning, by the processor, one or more patient partner-variables to each of the patient partners;

storing, by the server memory, one or more queries assigned to the one or more patient partner-variables;

transmitting to the client computer the one or more queries assigned to the one or more patient partner-variables; and receiving, by the processor, one or more data inputs from the client computer in response to the one or more queries assigned to the one or more patient partner-variables, wherein the list of patient partners is generated as a function of the data inputs from the client computer in response to the one or more queries assigned to the one or more patient partner-variables.

14. The method according to claim 13, wherein the one or more patient partner-variables comprise at least one of patient gender, patient age, patient height, patient weight, patient ideal weight, and patient preexisting conditions.

15. The method according to claim 13, wherein the one or more patient partner-variables comprise at least one of a patient's surgical experience, patient's preoperative status, preferred gender of patient partner, patient age, and patient activity level.

* * * * *